(12) United States Patent
Fleischer (10) Patent No.: US 7,648,485 B2
(45) Date of Patent: Jan. 19, 2010

(54) PLASTER DEVICE FOR SUPPORTING A BENDED LENGTH OF A TUBE

(75) Inventor: Philip Fleischer, Copenhagen S (DK)

(73) Assignee: Lina Medical ApS, Glostrup (DK)

( * ) Notice: Subject to any disclaimer, the term of this patent is extended or adjusted under 35 U.S.C. 154(b) by 267 days.

(21) Appl. No.: 11/518,568

(22) Filed: Sep. 8, 2006

(65) Prior Publication Data

US 2007/0049871 A1 Mar. 1, 2007

Related U.S. Application Data (63) Continuation-in-part of application No. PCT/EP2005/002677, filed on Mar. 14, 2005.

(30) Foreign Application Priority Data

Mar. 12, 2004 (DK) ................................ 2004 00406

(51) Int. Cl.
*A61M 5/32* (2006.01)
(52) U.S. Cl. ..................................... 604/174
(58) Field of Classification Search ......... 604/174–180, 604/250, 161, 164.01
See application file for complete search history.

(56) References Cited

U.S. PATENT DOCUMENTS 2,669,231 A * 2/1954 Fisher ........................ 604/179

| 4,579,120 | A | * | 4/1986 | MacGregor | 600/392 |
| 5,224,935 | A | * | 7/1993 | Hollands | 604/180 |
| 5,616,131 | A | * | 4/1997 | Sauer et al. | 604/174 |
| 5,637,098 | A | * | 6/1997 | Bierman | 604/180 |
| 5,685,859 | A | * | 11/1997 | Kornerup | 604/180 |
| 5,941,856 | A | | 8/1999 | Kovacs et al. | 604/179 |
| 6,375,639 | B1 | | 4/2002 | Duplessie et al. | 604/174 |
| 7,547,296 | B2 | * | 6/2009 | Lampropoulos et al. | 604/180 |

FOREIGN PATENT DOCUMENTS

EP 0463 718 A1 1/1992
WO WO 98/10823 3/1998

* cited by examiner

*Primary Examiner*—Matthew F Desanto
(74) *Attorney, Agent, or Firm*—Winston & Strawn LLP (57) ABSTRACT

A plaster device serves for fixating a length of a medical tube in relation to a skin surface of an individual having said tube inserted into a body part via an opening. The plaster device is of the kind including an adhesive part having an upper side, an adherent lower side for attaching the plaster device to the skin, and a through-opening for receiving the tube, a support part at least partly attached to the upper side of the adhesive part and arranged for supporting a bent length of said inserted tube, and fastenings means for securing the tube on the support part. The support part is an integral unit having a branched-off portion defining at least one recess for accommodating at least a part of a fastening means, preferably elastic means. A frictional force between the tube and the fastening means guarantees that the tube is prevented from moving or displacing to cause patient discomfort. The convex shape of the upper supporting surface provides a smooth anti-kinking support and guidance for the bended tube.

19 Claims, 8 Drawing Sheets

PLASTER DEVICE FOR SUPPORTING A BENDED LENGTH OF A TUBE

CROSS-REFERENCE TO RELATED APPLICATIONS

This application is a continuation-in-part of International application no. PCT/EP2005/002677 filed Mar. 14, 2005, the entire content of which is expressly incorporated herein by reference thereto.

FIELD OF INVENTION

The present invention relates to a plaster device for fixating a length of a medical tube in relation to a skin surface of a patient having said tube inserted into a body part via an opening in the skin surface.

The plaster device is of the kind that includes an adhesive part having an upper side, an adhered lower side for attaching the plaster device to the skin surface, and a through-opening for receiving the tube, a support part partly attached to the upper side of the adhesive part and arranged for supporting a bended length of said inserted tube, and fastenings means for securing the tube on the support part.

BACKGROUND OF THE INVENTION

Medical tubes are often introduced into a wound, a cavity or an organ of a human or animal body to facilitate sustained drainage or sustained supply of liquid or gaseous substances. Examples of medical tubes used for drainage include, but are not limited to, a chest drainage tube, a lumpectomy or a mastectomy drainage tube, a renal drainage tube for use in e.g. dialysis or percutaneous nephrostomy, and a drainage tube for emptying e.g. an encystment or an abscess. Examples of medical tubes used for supplying a substance to the patient include, but are not limited to, tubes and catheters for controlled administration of palliatives, such as analgesia, and hormones, such as insulin, delivered via e.g. an insulin pump. Proper securing of the medical tube at and in relation to the patient's skin is necessary to improve the patient's comfort during the treatment. It is of outmost importance to avoid contamination of the puncture site, to avoid dislodgement of the tube, e.g. during inspection of the puncture site or during the patient moving, and to avoid kinking, blocking or obstruction of the tube to prevent discontinuity of drainage or supply.

Traditionally, a medical tube inserted into the patient through an incision in the skin is fixated by means of sutures at the incision site. Such sutures leaves scars and may even serve as wicks for undesirable contamination of the incision and the skin around the incision site. To prevent such contamination and to improve securing of the tube, a plaster strapping can be attached to both the skin and around the tube adjacent the incision.

DESCRIPTION OF THE PRIOR ART

Several approaches have been made to improve this securing technique, which is very distressing to the patient. Nowadays, more sophisticated techniques are used due to improved plaster devices and skin-friendly adhesives.

An improved catheter retainer has been suggested in British patent document GB 2,288,530. The retainer can be adhesively secured to a patient's skin at the incision site to hold an introduced catheter in a fixed position. The retainer allows the catheter to be bent through a right angle as the catheter exits the patient without it kinking. The catheter is kept in place in the bent position in a slot by means of a clamp, which compresses and clamps the catheter into the slot. This device has uncomfortable rigid parts protruding from the patient's skin and the patient's clothes may be caught on the clamp, which accordingly will release the catheter. Another disadvantage is that it is impossible to inspect the incision site and consequently it is impossible to obtain information regarding infection at the site and/or leakage through the incision.

A plaster device without any substantially rigid parts is known from International patent application WO 95/33508. This known device has a plaster component for attaching the device to the skin of the patient and a support component for supporting a tube inserted into the patient's body via an incision in the skin. The tube is supported on the support component such that the tube changes orientation from an orientation substantially perpendicular to the patient's skin to an orientation substantially parallel to the patient's skin. The tube is fixated in this bent use-position by means of an adhesive securing strip applied sealingly over the tube and the support component. It is possible to inspect the tube and the site of the incision if the securing strip is transparent. However, it is impossible to obtain a reliable and convincing overview of the condition around the entire site of incision without removing the securing strip. Since the tube is not sutured to the incision site it is difficult to ensure that the tube is not displaced during removal of the adhesive securing strip. Consequently, this manipulation of the securing strip may displace the tube resulting in discomfort for the patient. In addition, the tube is covered with adhesive residues and will inadvertently stick to any adjacent component. Due to this disadvantage, the nurse is not inclined to perform as many inspections as are needed in order to be completely sure that e.g. no bleeding, infection or allergic reaction appears around the incision site, a part of which is hidden by the bent tube.

This prior art document further discloses an alternative embodiment proposing a securing strap for fixating the tube in the use-position. The support part of this embodiment consists of three individual elements: two side elements of a soft foamed material attached on each side of a central element of a hard or rigid foamed material. A groove serving for preventing displacement of the tube is defined by the upper side of the central element and the sides of the side elements adjacent the central element. The combined support part is attached to the underlying plaster component so that the securing strap is arranged around the central element. This structure has the disadvantage that during tightening of the strap, there is a risk that the central element will be detached from any of the elements surrounding it and as a consequence destroy the entire structure.

From European patent EP 0 463 718 B1 is known a catheter retainer as a means to avoid stitching of the catheter to the skin of the wearer. EP 0 463 718 B1 discloses a plaster device having protruding ears. The catheter is exteriorised between said ears and at a very short section the catheter is secured to the ears by means of a thread. The thread is wound around both the ears and the catheter using a number of winds to make sure that the catheter is not displaced when the patient moves. The use of this known device includes a considerable risk that the thread gets tangled up during winding and as a result the thread is complicated to unwind. Moreover, when arranging the thread around the catheter care must be taken not to clamp the catheter together. To avoid this often a rather loose winding is applied to the catheter resulting in that the catheter can slide back and forth with great discomfort to the patient as a result. Moreover this known device does not provide support for a bended length of a tube.

Accordingly, there are needs in the art for improved devices of this type.

SUMMARY OF THE INVENTION

It is a first aspect according to the present invention to provide a simple and inexpensive plaster device for improved fixation on a patient's skin of a medical drainage or supply tube.

It is a second aspect according to the present invention to provide a plaster device for fixating a medical drainage or supply tube on a patient's skin in a use-position, in which kinking, blocking, compressing or obstruction of the tube is prevented.

It is a third aspect according to the present invention to provide a plaster device, which is easy to apply and use, and provides a comfortable and convenient fixation of a medical drainage or supply tube on a patient's skin.

It is a fourth aspect according to the present invention to provide a plaster device, which does get caught in the surroundings, e.g. the patient's clothes.

It is a fifth aspect according to the present invention to provide a plaster device for preventing a medical drainage or supply tube inserted through a patient's skin from displacing after fixation and during movement of the patient.

The novel and unique features whereby this is obtained is the fact that the support part is an integral unit having a branched-off cleat-shaped portion defined by at least one recess in the support part for accommodating at least a part of the fastening means.

Thus, the invention relates to a plaster device comprising

BRIEF DESCRIPTION OF THE DRAWING FIGURES

The invention will be further described below with reference to the drawings showing examples of embodiments for a plaster device according to the present invention, in which.

DESCRIPTION OF A PREFERRED EMBODIMENT OF THE INVENTION

As used herein the term "cleat-shaped" is to be understood as an element having a shape and function substantially similar to a cleat on e.g. boat. In the context of the present application "cleat-shaped" therefore means an element having a stem with protruding portions around which a fastening means can be twisted for securing an object.

By designing the support part as an integral unit the risk of the support falling apart during fastening of the tube with the fastening means is eliminated.

In a preferred embodiment the support part has two opposite facing recesses, one on each side of the longitudinal center axis of the support part. These recesses branch off from the support part, a first and a second fastening flap or arm which together define a cleat-shaped portion on the support part. Preferably the support part may have an elongated configuration with a substantially convexly curved upper supporting surface for supporting the tube in the use-position. Preferably, the upper supporting surface includes the topside of the cleat-shaped portion and constitutes an advantageous smooth supporting surface for supporting in an anti-kinking manner the length of the tube bent through a right angle.

It is preferred that the support part is made of a foamed material, which is substantially dimensionally stable, so that it will substantially keep its shape when the plaster device is used, and is so flexible that it will yield without compressing the supported tube if the patient bump or press against something.

Moreover, the recesses constitute a perfect means for accommodating a detachable fastening means, which is used for lashing or anchoring the tube into a secured relationship with the supporting surface. Once the tube is secured with the fastening means, movement or displacement of the tube is impossible because the arms will clamp around the fastening means in a flexible and frictionally manner.

A further advantage exists in that the fastening means can easily be loosened and disengaged from the recesses. Since no adhesive is involved no adhesive remains settles on the fastening means. The tube may, if needed or desired, be carefully lifted so that areas otherwise not inspectable, such as e.g. the incision site hidden between the bent tube and the support part, can be inspected and treated sufficiently early to prevent damages.

If occasion should render it necessary and appropriate, the tube may even be substituted by a new tube without change of the plaster device in use. No physical adherence exists between the inserted tube and the fastening means and the securing capability is not lost or reduced by simply detaching the fastening means as with the prior art devices.

The cleat-shaped portion can be more or less protruding to accommodate various types of fastening means thicknesses and the outer shape may also within the scope of the present invention be given any configuration generally having a stem and a head, e.g. a mushroom-like configuration. The length of the stem is decisive for providing a securing space recess of a certain size. A too long stem would tilt and does not provide any clamping effect. A too short stem leaves no room for the fastening means and makes it very difficult to place the fastening means correctly.

In the preferred embodiment the fastening means is made of an elastic, flexible, resilient or springy material, preferably having a memory, the fastening means is easy and expeditious to apply around the tube for carefully fastening the tube against the support part without compression of the tube's lumen. A simple band or strap of rubber, silicone or polyurethane has been found especially fit for use, but straps, bands or laces can also be used. For the comfort of the patient it is preferred that the material of the fastening means is selected so that the frictional force between the material of the tube and the material of the fastening means is sufficiently high to prevent mutual dislocation or displacement of the fastening means and the tube in relation to each other. If the fastening means is detachably arranged in relation to the support part and the adhesive part, the fastening means can easily be substituted with a new fastening means without having to change the entire plaster device.

Prior art devices for similar purposes have no fastening means, which in a similar simple reliable manner can provide friction to prevent displacement.

Although it is preferred that the fastening means is detachable, it is obvious to the skilled person that a part of the fastening means used in the present invention can quite as well be permanently attached to a part of the plaster device.

A cover means can advantageously be provided for protection of the inserted tube, which rests secured on the support part of the plaster device. In a preferred embodiment the cover part may consist of a first cover part arranged for coupling together with either a second cover part attached to at least a section of the upper side of the adhesive part or for just coupling or adhering to the upper side of the adhesive part itself. The risk of infection is considerably reduced because the first and second cover parts when joined together completely enclose the entire support part, the supported length of the tube and the incision site.

In a very simple preferred embodiment the first cover part is a sheet of textile, preferably entirely made of a VELCRO® hook and loop fastener or made of a textile having a VELCRO® hook and loop fastener strip provided along the perimeter. The sheet must have an area sufficiently large to cover at least the support part in the use position. It is preferred that the textile is air permeable so that humidity is allowed to evaporate and humidification is avoided. The VELCRO® sheet is preferably fully detachable but can alternatively be connected to any portion of the adhesive part e.g. an edge or a rim. The VELCRO® sheet may have a smooth outside so that the plaster device not does catch the patient's clothes or other surrounding protruding elements.

The second cover part for coupling together with the first cover part can be a circumferential VELCRO® hook and loop fastener strip attached to the upper side of the adhesive part along or a distance from the perimeter of this, and arranged for sticking to the first cover part. A preferred distance between the perimeter of the adhesive part and the outline of the second cover part could for example be between 1-25 mm depending on the size of the adhesive part.

In a preferred embodiment according to the present invention the first cover part is smaller than the adhesive part, in which case the perimeter of the first cover part is coupled to the second cover part or the adhesive part at a distance from the perimeter of the adhesive part. This arrangement prevents the adhesive on the adhesive part to work loose its firm adhesive grip on the skin when the first cover part is move and manipulated during movement of the wearer. For some purposes it is alternatively preferred that either the side of the rim portion of the first cover part facing the adhesive part or the rim portion of the upper side of the adhesive part itself or both these portions may be glued in order to stick sealingly together.

The plaster device may also comprise at least one of the means selected from the group including absorbent agents or bactericides. Absorbing layers may additionally be added to the structure or inserted where needed. Absorbing layers may include, as the absorbent agent, a hydrocolloid, for further ensuring that the incision site is kept dry. Also pads or compositions including e.g. a bactericide, an antibiotic and/or an antifungal agent for killing any active bacteria or fungus may be included in the structure. Also a medicament can be included in the structure. The absorbent layers or pads may be of any convenient material known to the person skilled in the art, e.g. cellulose webs, porous pads, non-woven materials, etc.

In a very simple embodiment of a plaster device according to the present invention for fixating a length of a medical tube in relation to a skin surface of an individual having the tube inserted into a body part via an opening, the plaster device is essentially the very support part described above. This support part serves for supporting a bent length of the inserted tube; the support part is an integral unit having a branched-off cleat-shaped portion defining at least one recess, preferably two recesses, for accommodating at least a part of a fastenings means for securing the tube on the support part.

The adhesive part for attaching the plaster device to the skin surface of an individual of the previously described embodiments of plaster devices may in this third, very simple embodiment be an adhesive on at least a part of the underside of the support part opposite the convexly curved upper supporting surface. Such an adhesive may e.g. be an adhesive layer covering the entire underside or scattered adhesive sections or dots. Preferably said adhesive is covered with a cover foil to be removed when the plaster device is to be used.

Within the scope of the present invention the plaster device can alternatively be attached to the skin surface by means of an adhesive tape overlaying the support part and connecting the support structure to any substructure, e.g. the skin surface of the patient. However, this simple embodiment is also suitable for, in an easy manner, directing and fixing a tube in a non-kinking relationship to e.g. a drop stand, a mattress, mat, cushion or any other relevant substructure. A plaster according to third embodiment but without an adhesive on the underside may be anchored to the substructure by means of a strip of tape or any other suitable means.

The design of the support part corresponds to the design of the support part previously described. Accordingly, the support part also has two opposite facing recesses, one on each side of the longitudinal centre axis of the support part, and an elongated configuration with a substantially convexly curved upper supporting surface for supporting the tube in the use-position. The tube may be secured to the support part using a fastening means made of an elastic, flexible, resilient or springy material, preferably a band or strip of rubber, silicone or polyurethane, which preferably also is detachably arranged in relation to the support part. A short length of the medical tube is shown in the figures for illustrative purposes only.

Also, the adhesive part is shown to be rectangular, however other geometrical outlines such as e.g. oval or circular are also within the scope of the present invention.

The area of the adhesive part exceeds the base area of the support part, and the adhesive part's through-opening for the tube is located at a distance from the perimeter of the adhesive part in order to provide space for the joining of the cover parts.

Figure 1:
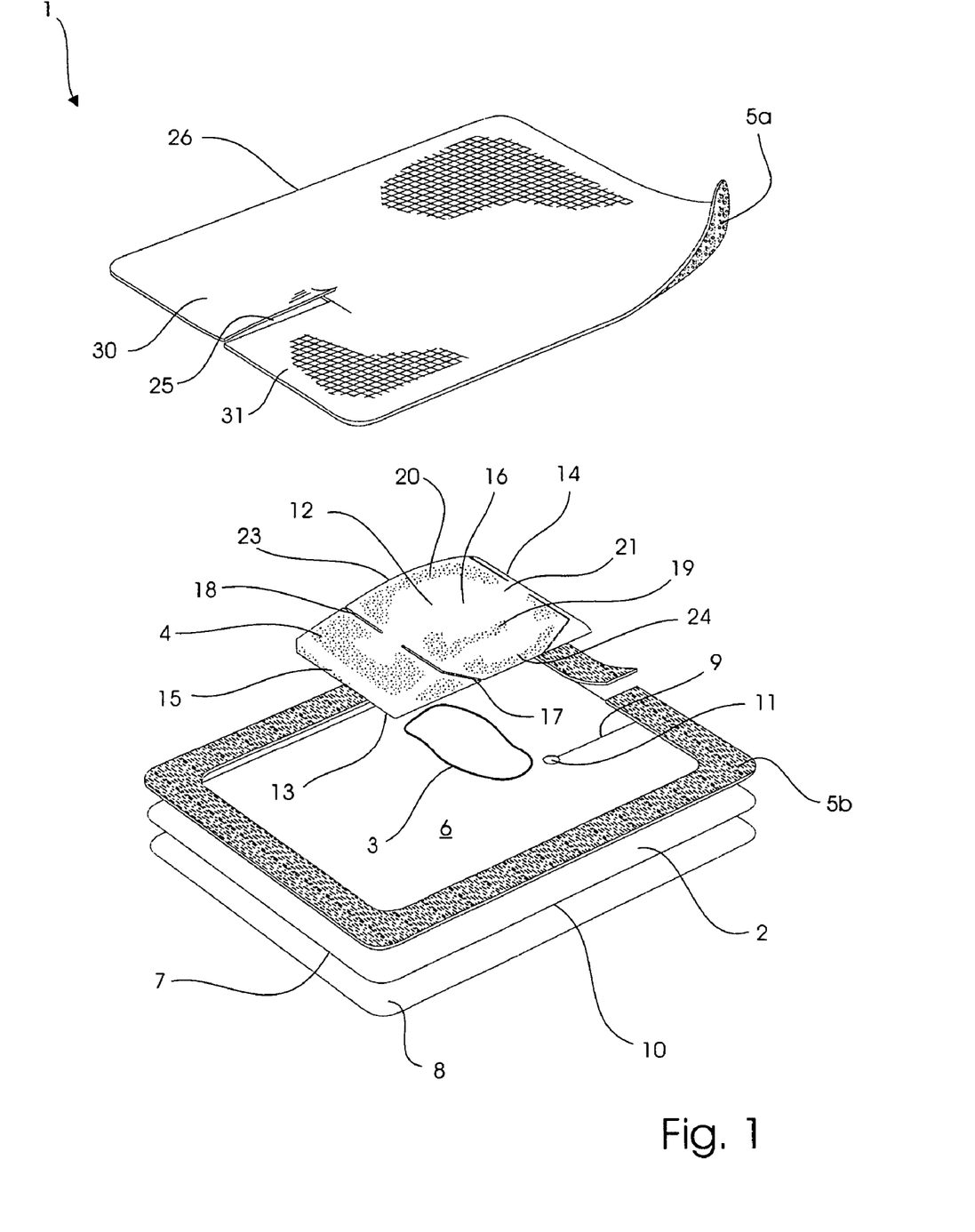
FIG. 1 is an exploded view of the elements of a first embodiment of a plaster device according to the present invention, FIG. 2 schematically shows the plaster device in FIG. 1 applied on a skin surface in relation to an inserted tube at a first step of the fixation procedure before the tube is fixated on the support part.

The elements of the plaster device 1 are shown in the exploded view of FIG. 1. The plaster device is composed of four main elements: an adhesive part 2, a fastening means 3, a support part 4 and a cover part 5. The adhesive part 2 has an upper side 6 and an adherent bottom side 7, the adhesive of which is protected with a detachable sheet of protective foil 8. The adhesive part 2 has a slit 9 extending a distance from the perimeter 10 of the adhesive part 2 into said adhesive part 2 for meeting a through-opening 11 for the tube 27 in the use-position shown in FIGS. 3-6. The slit 9 and through opening 11 for the tube, does not necessarily have to extend all the way into the support part 4, but could stop a distance from the support part 4.

The fastening means 3 is an elastic band 3 having a circular cross-section. However, other cross-sections such as rectangular or quadratic may be preferred for some uses, since they may provide a better friction against the tube's outer surface. The fastening means 3 is interposed between the adhesive part 2 and the support part 4.

The support part 4 has a convexly curved upper supporting surface 12 for supporting the tube in the use-position and an underside 13. The support part 4 is divided into a front-end part 14, a rear-end part 15, and a central portion 16 by means of two opposite facing recesses 17,18. The recesses branch-off from the support part the central, cleat-shaped portion 16 with two diametrically opposite arms 19,20. The central portion 16 is integral with the front-end part 14 and the rear-end part 15 at a longitudinal central section 21 along the longitudinal centre axis A of the support part 4. The front-end part 14 is attached to the upper side 6 of the adhesive part 2 adjacent the through-opening 11. The rear-end part 15 is similarly attached to the adhesive part 2 distal from the through-opening 11 so that a channel 22, extending between the parallel sides 23,24, is created below the central portion 16.

The cover part 5 consists of a first cover part 5a and a second cover part 5b. The first cover part 5a is, in the embodiment shown in the figures, a rectangular VELCRO® sheet having substantially the same or slightly greater area as compared to the adhesive part 2. The adhesive part is preferably made of a transparent material allowing inspection of the skin surface underneath it. In this case the second cover part 5b must not cover the entire adhesive part 2. Hence, the second cover part 5b is preferably a rectangular strip 5b, also made of VELCRO®. The narrow VELCRO® strip 5b is attached along the perimeter 10 of the adhesive part 2 on the outer rim portion of said adhesive part 2 e.g. by means of an adhesive and faces the first cover part 5a. The ends of the strip 5b meet at opposite facing sides of the slit 9. Due to the narrow width of the second cover part 5b, a central area of the adhesive part 2 remains uncovered. Inspection of the underlying skin surface is therefore still possible.

The cover parts 5a,5b can firmly and detachable be joined together by VELCRO® attachment. The cover parts 5a,5b can have other types of adherent or sticky contact areas, such as e.g. glued contact areas covered by protective peelable foils. However, these alternatives are less preferred since such joinings are difficult to break and re-establish without damaging the adhesiveness of the cover parts 5a,5b or risking that the adhesive part 2 detaches from the skin surface to which the device 1 is attached. The first cover part 5a has a cover part slit 25, which extends a distance from the perimeter 26 of the cover part 5a into said cover part 5a. The slit 25 defines two opposite facing flaps 30,31 which together with the slit 25 serve for guiding the bent length of the tube 27 and for holding the tube 27 substantially parallel with the subjacent skin surface (not shown).

Figure 2:
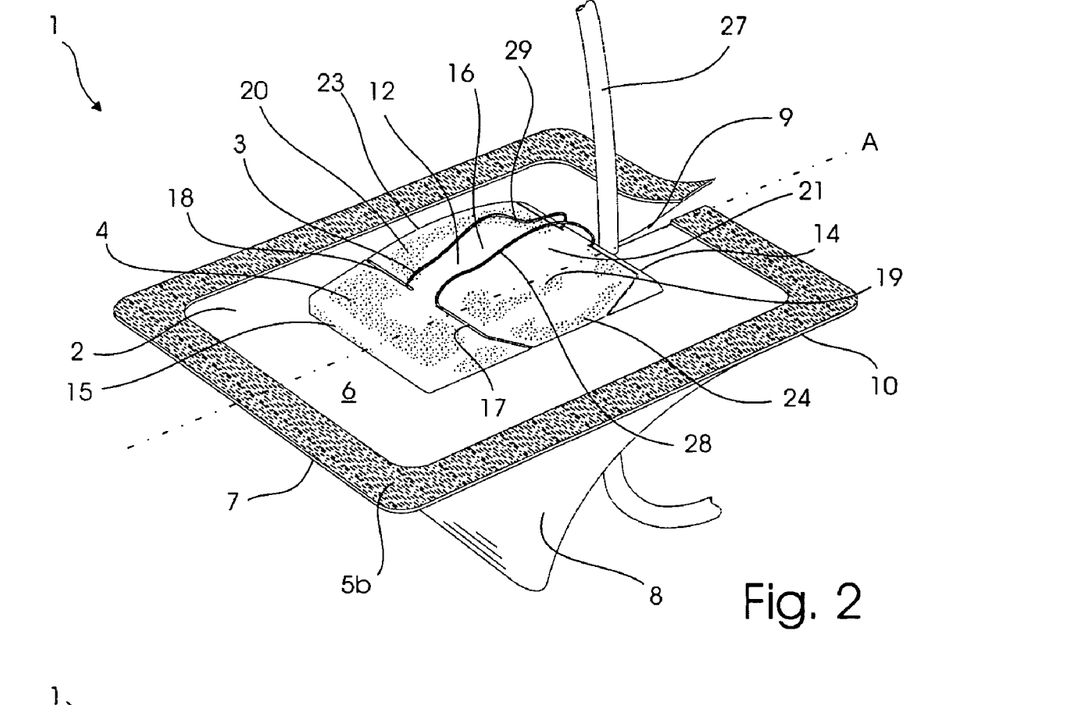

FIG. 2 shows the plaster device 1 according to the invention with the through opening 11 of the plaster device 1 located around the tube 27. The protective foil 9 is shown partly detached from the adherent bottom side 7 of the adhesive part 2. A substantially flat narrow elastic band 3 is placed in the channel 21 between the support part 4 and the adhesive part 2 and passed into opposite recesses 17,18 and around the arms 19,20, thereby forming two fastening loops 28,29.

Figure 3:
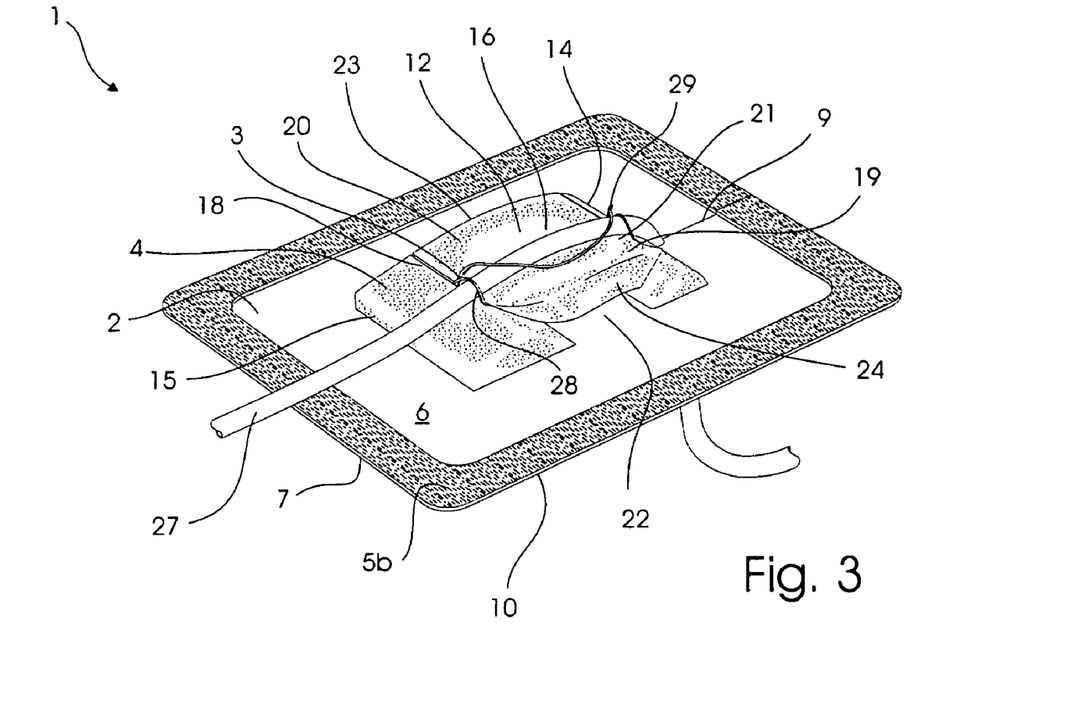
FIG. 3 shows schematically a second step of the fixation procedure, in which the tube is bent through a right angle and partly fixated on the support part.

As best seen in FIG. 3 the tube 27 is bent into a right angle until the tube rests firmly on the convexly curved upper supporting surface 12 of the support part 4. The change of angle of the inserted tube 27 takes place when the tube is bent from a first position in which the tube is inserted via the incision site substantially perpendicular to the patient's skin, to a second position substantially parallel to the patient's skin, in which the bent length of the tube rest on the convexly curved upper supporting surface 12 of the longitudinal central top section 21 of the support part 4.

In FIG. 3 the fastening loop 28 has already been passed across the tube 27 and is situated in the recess 18 securely around the arm 20. Laterally reverse of the fastening loop 28, the fastening loop 29 is shown in the process of crossing in over the tube 27 for being situated in the opposite recess 17 in a manner corresponding to the one for the fastening loop 28.

Figure 4:
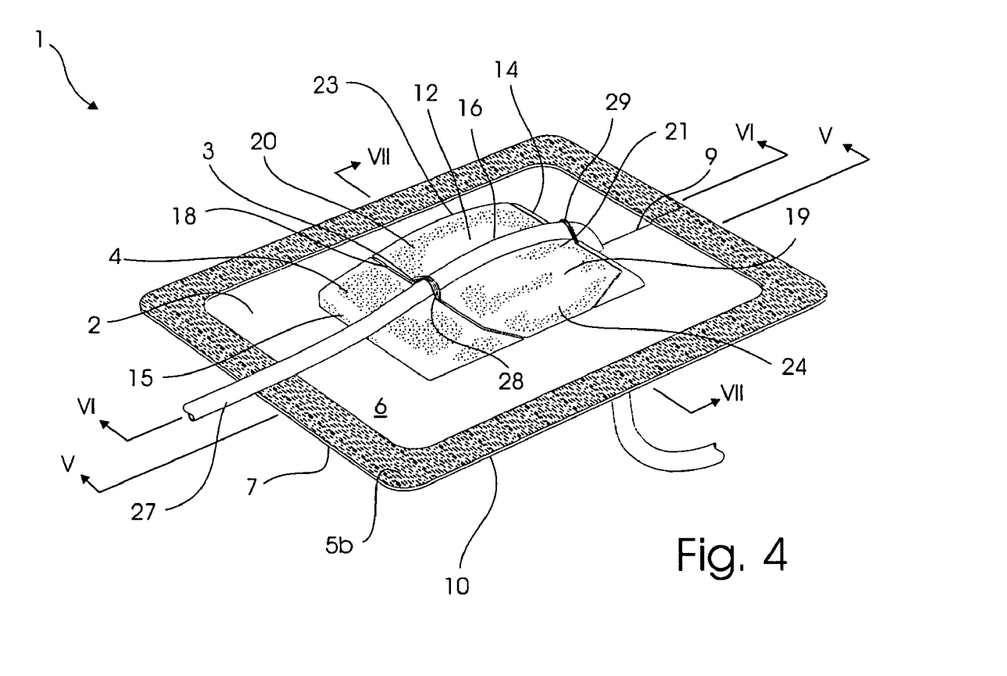
FIG. 4 shows a third step of the fixation procedure, in which the fastenings means is fully fastened around the tube.

As illustrated in FIG. 4 both the elastic fastening loops 28,29 are now situated around the arms 20,19 in respective opposite recesses 18,17, and the bent length of the tube 27 is firmly anchored by the crossed fastenings loops on the upper supporting surface 12 of the support part 4. Due to the chosen elasticity of the fastening means, the lumen of the tube is never squeezed. A frictional force between the tube and the fastening means guarantees that the tube is prevented from moving or displacing. No stitches at the incision site or grooves or depressions in the support part are required for holding the tube in place. However, such means can be used if considered expedient.

Figure 5:
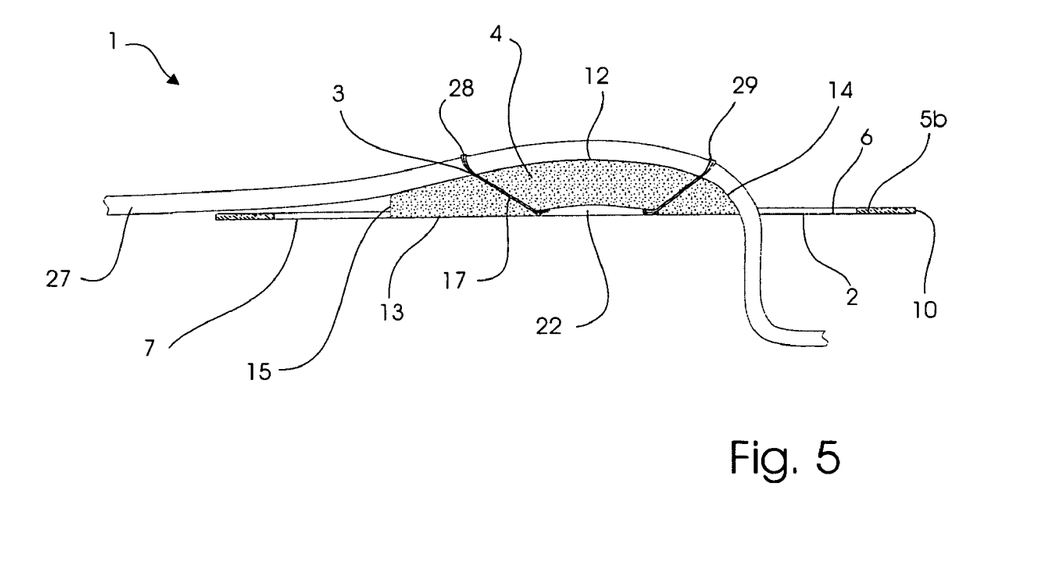
FIG. 5 shows a longitudinal section along the line V-V in FIG. 4, FIGS. 6 and 6a show a longitudinal section along the line VI-VI in FIG. 4.

At seen better in FIG. 5 the convex shape of the upper supporting surface 12 provides a smooth anti-kinking support and guidance for the tube 27, which is bended via a right angle from a position substantially perpendicular to the patient's skin to the position substantially parallel to the patient's skin. The fastening means 3 passes through the channel 22, and extends into the crossed fastening loops 28,29.

Figure 6:
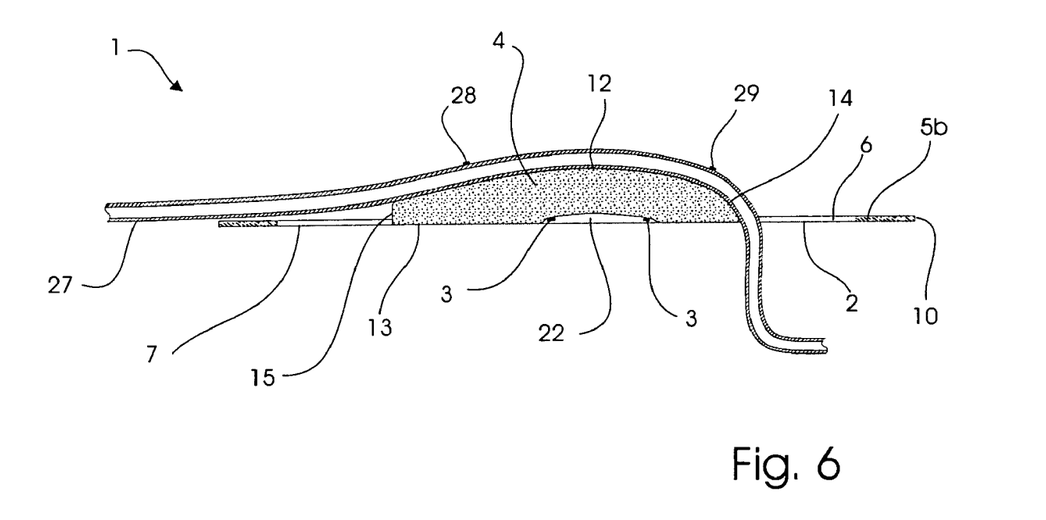
Figure 7:
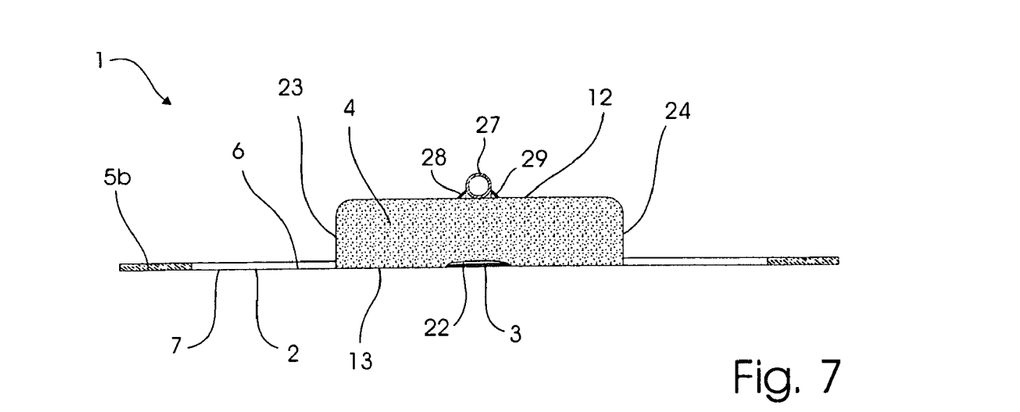
FIG. 7 shows a cross-section along the line VII-VII in FIG. 4.

FIG. 6 shows a section along the line VI-VI in FIG. 4 and illustrates how the fastening loops 28,29 passes in the channel 22 underneath the support part 4. FIG. 6 also demonstrates that the support part is an integral unit along the central part 16 of the support part 4, and FIG. 7 demonstrates the transverse integrity of the support part.

Figure 6A:
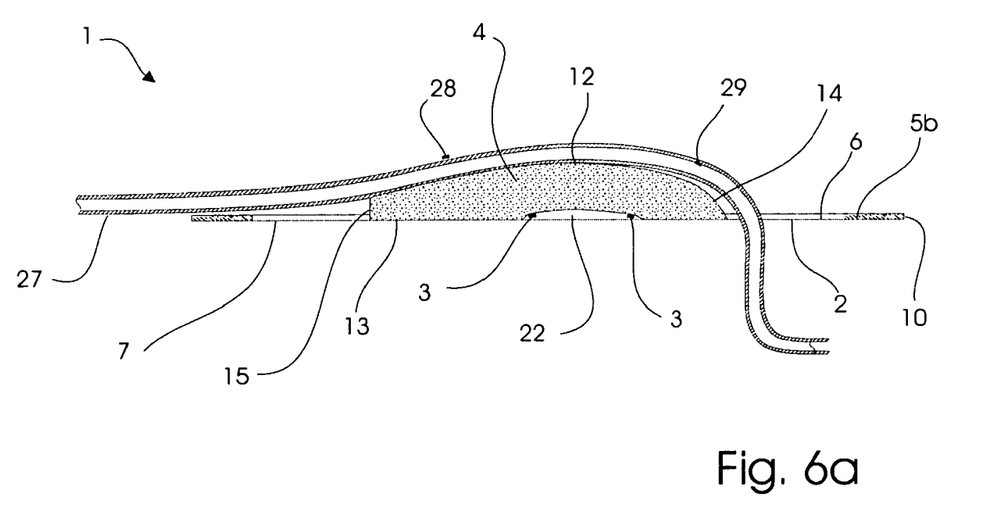

The embodiment shown in FIG. 6a corresponds substantially to the embodiment shown in FIG. 6 and for like parts same reference numeral are used. The embodiment shown in FIG. 6a is e.g. especially suitable for relatively thick tubes, such as pleural drainage tubes, which have a tendency to kink if bent too much. In order to prevent this, the opening and slit is situated a distance from the front part of the support part so that bending of the tube into supported relationship on the support part takes place in a smooth way.

Figure 8:
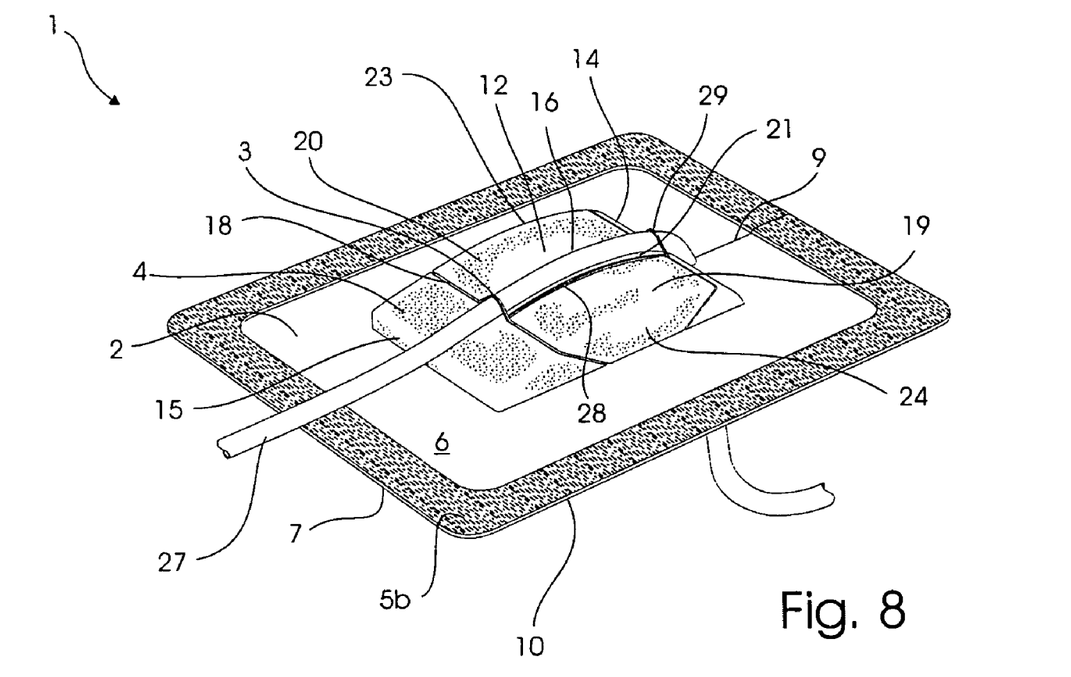
FIG. 8 shows an alternative way of application of the fastening means around the tube.

FIG. 8 shows a preferred way of fastening the fastening means 3. The fastening means 3 is before use arranged as shown and described for FIG. 2. Now, instead of crossing over the fastening loops 29,28 for fastening around respective opposite arms 19,18 only one of the loops is crossed over the tube. Hence, by pulling the fastening loop 29 for anchoring around the opposite arm 19 the other fastening loop 28 is tightened around it's adjacent arm 19 on the central portion 16 of the support part 4 substantially parallel to the tube 27. This way of fastening prevents the arms 18,19 from being lifted up above the tube 27 in the resting position of the tube 27 on the longitudinal central section 21.

Figure 9:
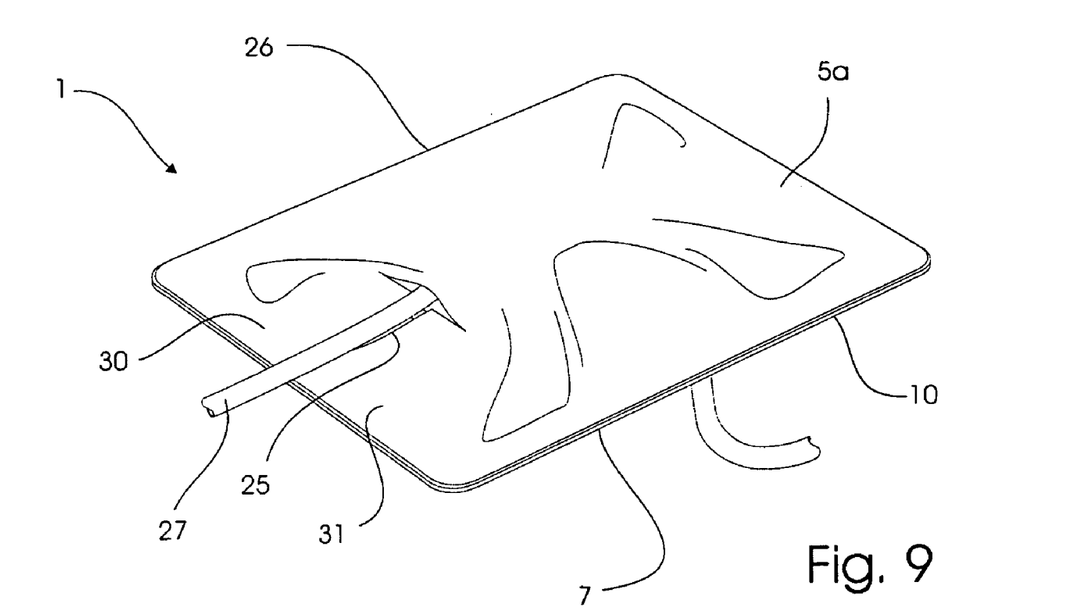
FIG. 9 shows a fourth step of the fixation procedure in which the first cover part is coupled to the second cover part for enclosing the bent length of the tube.

In FIG. 9 the first cover parts 5a are finally arranged over the supported tube and joined by VELCRO® attachment to the second cover part 5b for fully enclosing the supported tube. The tube is exteriorised from the first cover part 5a via the slit 25 and the flaps 30,31 are arranged underneath the exteriorised part of the tube and joined by VELCRO® attachment to the second cover part 5b. The first cover part 5a can easily be detached from the second cover part 5b in case inspection is needed. For example cleaning around the tube may be needed if leakage occurs around the tube or bleeding sets in at the incision site.

Figure 10:
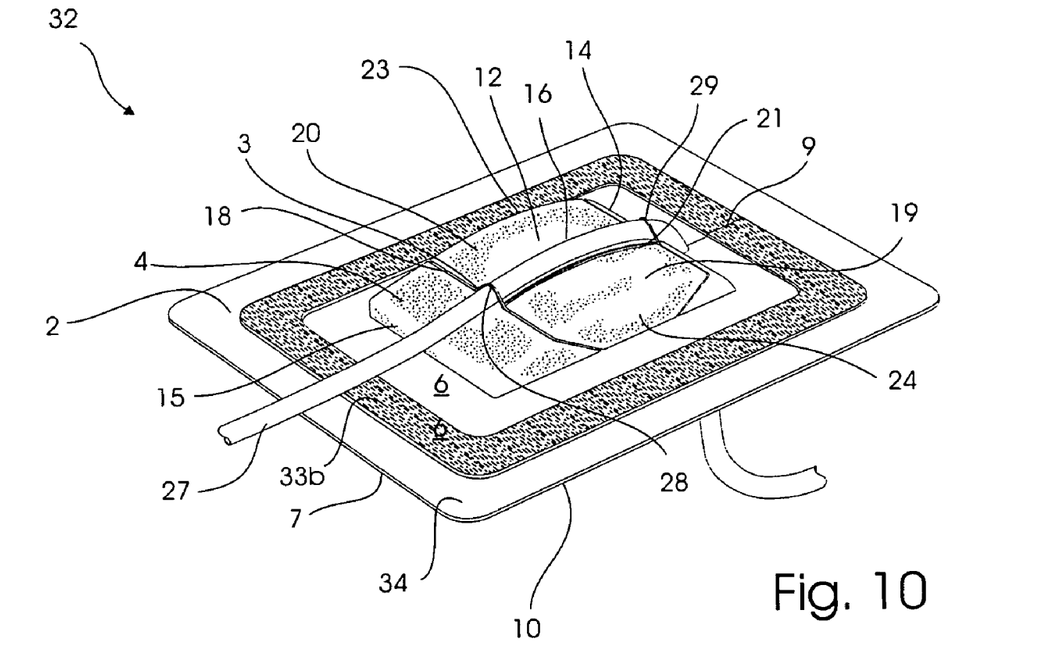
FIG. 10 shows a perspective view of a second embodiment of a plaster device according to the present invention.
Figure 11:
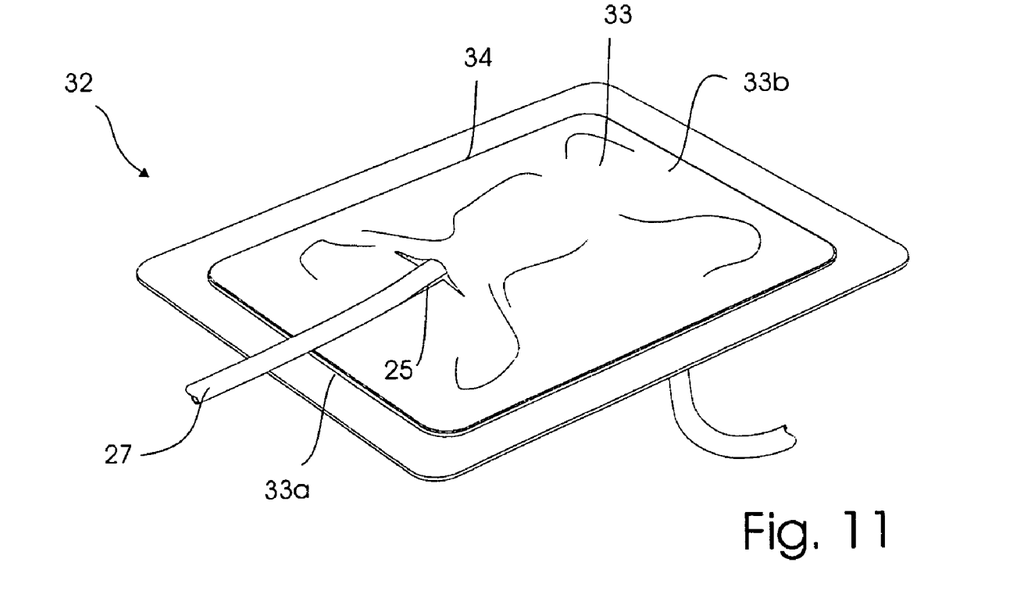
FIG. 11 shows the second embodiment covered with a cover means.

FIGS. 10 and 11 illustrate a second embodiment 32 for a plaster device according to the present invention. This plaster device 32 corresponds substantially to the first embodiment 1 and for like part are used same reference numbers. The plaster device 32 has an annular second cover part 33b surrounding the support part 4 but covering an area smaller than the area of the adhesive part 2.

In FIG. 11 the first cover part 33a is joined by VELCRO® attachment together with the second cover part 33b to enclose the support part 4 and the bended length of the tube. The second cover part has a smaller size than the size of the adhesive part to leave the outmost edge zone 34 of the adhesive part 2 free of covering to provide an edge zone 34 of resistance to drawing and movement forces and allow the plaster device 32 to maintain its firm adhesive attachment on the skin. This plaster device 32 provides optimum attachment conditions and a minimum risk of detachment when the wearer moves around.

Figure 12:
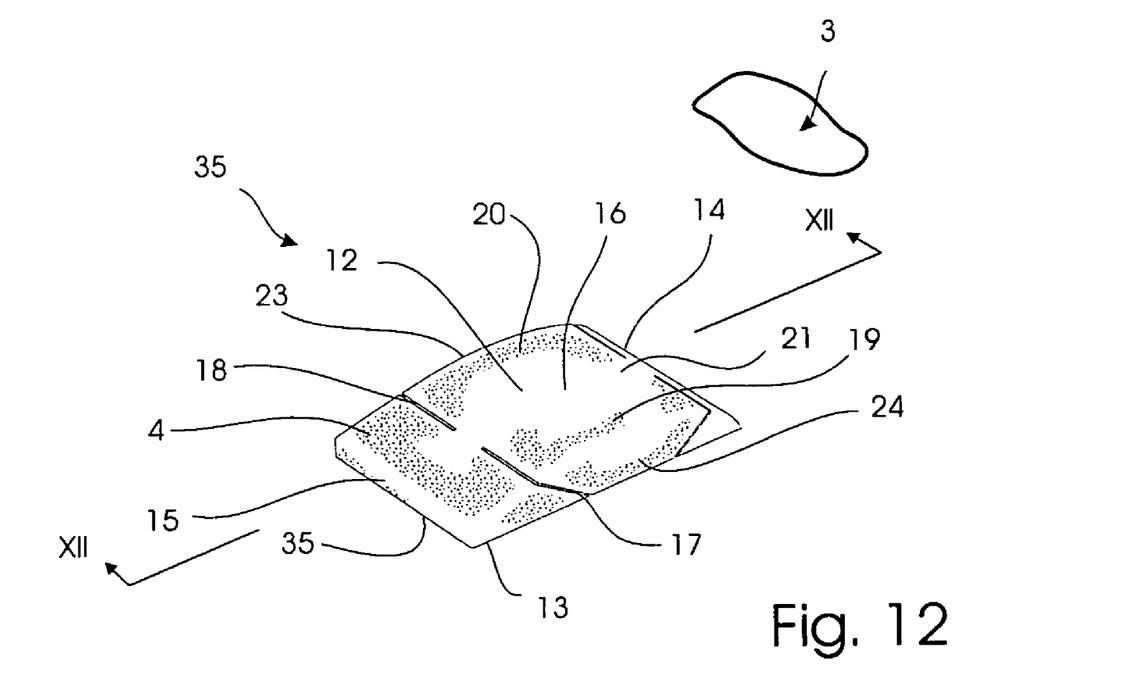
FIG. 12 shows a perspective view of a third, very simple embodiment of a plaster device according to the present invention.

FIG. 12 shows a third, very simple embodiment of a plaster device 35 according to the present invention. The plaster device 35 is comprised of the support part 4 and a fastening means 3 for securing a bent length of a tube inserted in a body of an individual (not shown), as described for the first and second embodiment of a plaster device according to the present invention, and for like part are used same reference numbers. The plaster device 35 has an adhesive 36 on the underside 13 facing opposite the convexly curved upper supporting surface 12 of the support part 4. As soon as the plaster device 35 is arranged on top of the skin surface adjacent the tube inserted into the opening in the patient the plaster device 35 functions just as the support part 4, as described above for the first and second embodiments of plaster devices 1;32.

Figure 13:
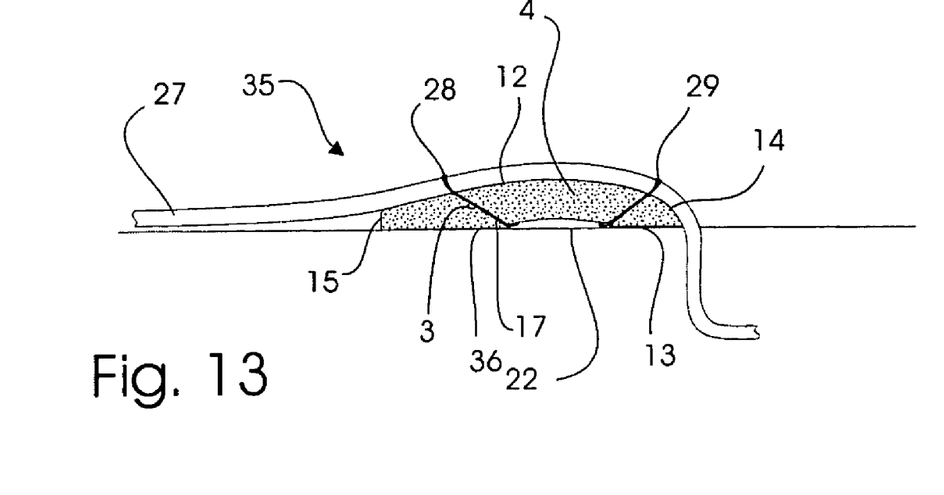
FIG. 13 shows a cross-section along the line XII-XII of the plaster device shown in FIG. 12 in use-position with a bent length of a tube.

As seen best in the cross-sectional view of FIG. 13 a channel 22, is created below the central portion 16 to provide accommodation for the fastening means 3. However, within the scope of the present invention adhesive may be provided on the underside 13 to an extent in which both the underside 13 of the support part 4 and the fastening means are entirely or partly adhered to the surface to which the plaster device are to be attached.

What is claimed is:

1. A plaster device for fixating a length of a medical tube in relation to a skin surface of an individual having the tube inserted into a body part via an opening, the plaster device comprising:
    an adhesive part having an upper side, an adherent lower side for attaching the plaster device to the skin, and an opening for receiving the tube,
    a support part having an elongated configuration and at least partly attached to the upper side of the adhesive part adjacent the opening, the support part positioned to accommodate an inserted tube having a portion that passes through the opening and a bent length extending over the support part, and having an upper supporting surface configured to support the bent length of said inserted tube in contact therewith, and
    means for securing the inserted tube interposed between the adhesive part and the support part;
    wherein the support part is an integral unit having a branched-off cleat-shaped portion defining at least one recess for accommodating at least part of the means for securing the tube on the support part.

2. The plaster device according to claim 1, wherein the plaster device further comprises a cover, including a first cover part arranged for coupling together with either a second cover part attached to at least a section of the upper side of the adhesive part or for coupling to the adhesive part itself.

3. The plaster device according to claim 2, wherein the first cover part is an at least partly detachable textile sheet, either entirely made of hook and loop fastener material or is provided with a strip of hook and loop fastener material the perimeter, and of an area sufficiently large to cover at least the support part in the use position, and the second cover part is an annular strip of hook and loop fastener material attached to the upper side of the adhesive part.

4. The plaster device according to claim 2, wherein the second cover part has a smaller size than the size of the adhesive part to leave an outmost edge zone free of covering.

5. The plaster device according to claim 1, wherein the support part has two opposite facing recesses, one on each side of the longitudinal centre axis of the support part.

6. The plaster device according to claim 1, wherein the support part comprises a foamed material and a substantially smooth and substantially convexly curved upper supporting surface for contacting and supporting the bent length of the tube in the use-position.

7. The plaster device according to claim 1, wherein the means for securing the tube is made of an elastic, flexible, resilient or springy material.

8. The plaster device according to claim 1, wherein the means for securing the tube is a band or strip of rubber, silicone or polyurethane.

9. The plaster device according to claim 1, wherein the means for securing the tube is detachably arranged in relation to the support part and the adhesive part.

10. The plaster device according to claim 1, further comprising at least one of an absorbent agent, a bactericide, a fungicide or a medicament.

11. The plaster device according to claim 1, wherein the adhesive part has a slit extending from the outer perimeter of the adhesive part to the opening.

12. The plaster device according to claim 1, wherein the branched-off cleat-shaped portion comprises two opposing arms and the means for securing the tube is interposed between the adhesive part and the opposing arms.

13. A plaster device for fixating a length of a medical tube in relation to a skin surface of an individual having the tube inserted into a body part via an opening, the plaster device comprising a support part having an elongated configuration and located adjacent the opening, the support part positioned to accommodate an inserted tube having a portion that passes through the opening and a bent length extending over the support part, and having an upper supporting surface configured to support the bent length of said inserted tube in contact therewith, wherein the support part is an integral unit having a branched-off cleat-shaped portion defining at least one recess for accommodating at least part of the means for securing the tube on the support part, and wherein the recess is smaller than the diameter of the tube.

14. The plaster device according to claim 13, wherein the support part has two opposite facing recesses, one on each side of the longitudinal center axis of the support part.

15. The plaster device according to claim 13, wherein the support part comprises a foamed material and a substantially smooth and substantially convexly curved upper supporting surface for contacting and supporting the bent length of the tube in the use-position.

16. The plaster device according to claim 13, wherein the means for securing the tube is made of an elastic, flexible, resilient or springy material.

17. The plaster device according to claim 13, wherein the means for securing the tube is a band or strip of rubber, silicone or polyurethane.

18. The plaster device according to claim 13, wherein the means for securing the tube is detachably arranged in relation to the support part.

19. The plaster device according to claim 13, wherein an adhesive is provided on at least a part of the underside of the support part.

* * * * *

UNITED STATES PATENT AND TRADEMARK OFFICE
CERTIFICATE OF CORRECTION

PATENT NO. : 7,648,485 B2 Page 1 of 1
APPLICATION NO. : 11/518568
DATED : January 19, 2010
INVENTOR(S) : Fleischer It is certified that error appears in the above-identified patent and that said Letters Patent is hereby corrected as shown below:

Title Page:
On the Title page, Item (56) References Cited, FOREIGN PATENT DOCUMENTS, insert the following reference:
-- WO 95/33508    12/1995 --

Signed and Sealed this

Sixth Day of July, 2010

David J. Kappos
*Director of the United States Patent and Trademark Office*